United States Patent [19]

van der Smissen et al.

[11] Patent Number: 5,036,842
[45] Date of Patent: Aug. 6, 1991

[54] RESPIRATOR WITH BLOWER SUPPORT AND REGENERATION OF THE BREATHING FILTER

[75] Inventors: Carl E. van der Smissen, Lübeck; Wolfgang Eckstein, Sereetz; Hans-Joachim Walther, Lübeck, all of Fed. Rep. of Germany

[73] Assignee: Dragerwerk Aktiengesellschaft, Lübeck, Fed. Rep. of Germany

[21] Appl. No.: 456,952

[22] Filed: Dec. 26, 1989

[30] Foreign Application Priority Data

Dec. 23, 1988 [DE] Fed. Rep. of Germany ....... 3843486

[51] Int. Cl.⁵ .................... A61M 16/00; A62B 18/02; A62B 9/02
[52] U.S. Cl. ................... 128/204.18; 128/204.21; 128/205.24; 128/205.25; 128/205.12; 128/201.25; 128/201.28
[58] Field of Search ............ 128/201.22, 201.23, 128/201.24, 201.25, 201.28, 204.26, 205.13, 204.18, 205.22, 205.25, 204.21, 205.12

[56] References Cited

U.S. PATENT DOCUMENTS

| 518,822 | 4/1894 | Moran | 128/201.23 |
| 544,832 | 8/1895 | Senior | 128/201.23 |
| 1,050,484 | 1/1913 | McGerry | 128/201.22 |
| 2,284,053 | 5/1942 | Hermann | 128/205.13 |
| 4,011,865 | 3/1977 | Morishita | 128/205.25 |
| 4,127,122 | 11/1978 | Kienhofer et al. | 128/201.25 |
| 4,233,972 | 11/1980 | Hauff et al. | 128/205.25 |

FOREIGN PATENT DOCUMENTS 7914929 10/1980 Fed. Rep. of Germany.
2058577 4/1981 United Kingdom.

Primary Examiner—David A. Wiecking
Assistant Examiner—Kimberly L. Asher

[57] ABSTRACT

A respirator with blower support for the flow through at least two filters in the breathing gas lead is provided such that the flow of one of the filters temporarily is in the inhalation direction and the other flow is in the exhalation direction respectively and their flow through direction is periodically reversible. This allows flow through of the filter in small volumes without a premature bursting or filter depletion. The wearer comfort should remain and the blower support is not diminished in its operation.

5 Claims, 2 Drawing Sheets

RESPIRATOR WITH BLOWER SUPPORT AND REGENERATION OF THE BREATHING FILTER

FIELD OF THE INVENTION

The invention concerns a respirator with blower support in a breathing gas lead.

BACKGROUND OF THE INVENTION

Respirators with filters that provide artificial breathing to a user, may encounter unwanted high breathing resistance due to the filter filling. It is known, that increased breathing stability may be attained through an an auxiliary blower or bellows (see GBN-A 2 058 577, DE-GM 7914 929). This way the resistance against the breathing function can be lowered to an imperceptible degree for the wearer of the apparatus. Since the breathing activity supported by a blower requires that a much larger quantity of air than actually needed be conducted through the filter in order to cover the person's need for breathable air during strenuous activities, large quantities of air continuously flow through the filter even when not needed for the support of the breathing function. For this reason the filters are subject to greater strain than necessay, which results in a premature rupture of the filters, thereby reducing the time of usage of the respirator. In order to increase the durability of the filters and prolong the time of usage of the respirators, it would be necessary to provide the filters with sufficient voluminous filter material. This would result in bulky devices which would be difficult to carry due to the heavy weight and its unwieldy volume.

SUMMARY AND OBJECT OF THE INVENTION

It is an object of the invention to provide a a respirator of the named type so that low volume air flow through the filter will not lead to a premature breaking through or a depletion of the filter while maintaining user comfort without diminishing breathing support.

According to the invention, it is provided that in each case one of the filters temporarily flows through in the exhalation direction and its flow direction is periodically reversible.

The advantage of the invention lies fundamentally in the utilization of the disorption properties of gases received from the inlet filter flowing in the exhalation direction. The filter loading will be at least partially decreased by the disorptive gases so that a certain regeneration of the filter material will be realized. By this arrangement, the gases flowing through in the inhalation direction will only pass through the contaminated inlet of the filter for a short time period. After the completion of the time period the flow will reverse direction and return through the filter (exhalation direction) so that the loaded filter will be cleansed by means of the exhalation air, whereby a large part of the received harmful substance will be desorbed and carried out the filter. During the desorption and cleansing period of flow in the exhalation direction, inhalation takes place through another filter, which now will be flowing in the inhalation direction and the harmful substance will be removed from the outside air prior to the air becoming part of the breathing supply of the device wearer. After the end of the regeneration time of the first filter another switching of the direction occurs so that the regenerated filter will again flow in the inhalation direction and the previously used filter flows through in the exhalation direction and will thus be regenerated. Through the alternate operation of the two filters respectively in the inhalation and exhalation direction, a periodic collection of the harmful substances and a cleansing of the filters through a blowing out into the surrounding air will be achieved.

With the invention, gasses having a low boiling point in particular which need only a small absorption capability of the filter and require light duty desorption will be effectively kept at a distance from the device carrier without needing a large capacity filter. Through the periodic desorption of this highly volatile material this type of filter can continually be regenerated. Without the reversal of the flowing through direction according to the invention an especially high filter capacity must be provided for such material.

An especially favored construction form of the invention consists in that both the inhalation branch and also the exhalation branch of the breathing gas are arranged to lead to blowers. The delivery of the blowers can be adjusted independently from each other (for the two branches), so that under the breathing supply breathing in and out can occur pressurelessly, whereby the breathing will be especially comfortable.

In order to avoid short delivery interruption during the switching time of the reversible blowers, it is provided, that the reversal of the flowing through direction will be realized through a switch valve in the autonomous breathing device. In this construction form the blower with its delivery can also work continually during the switching procedure, so that after the short switching time the desired output volume is immediately available.

In a further advantageous development of the invention, drying cartridges are connected between the filters and the breathing supply in order to prevent the filter from becoming excessively loaded through high exhalation moisture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
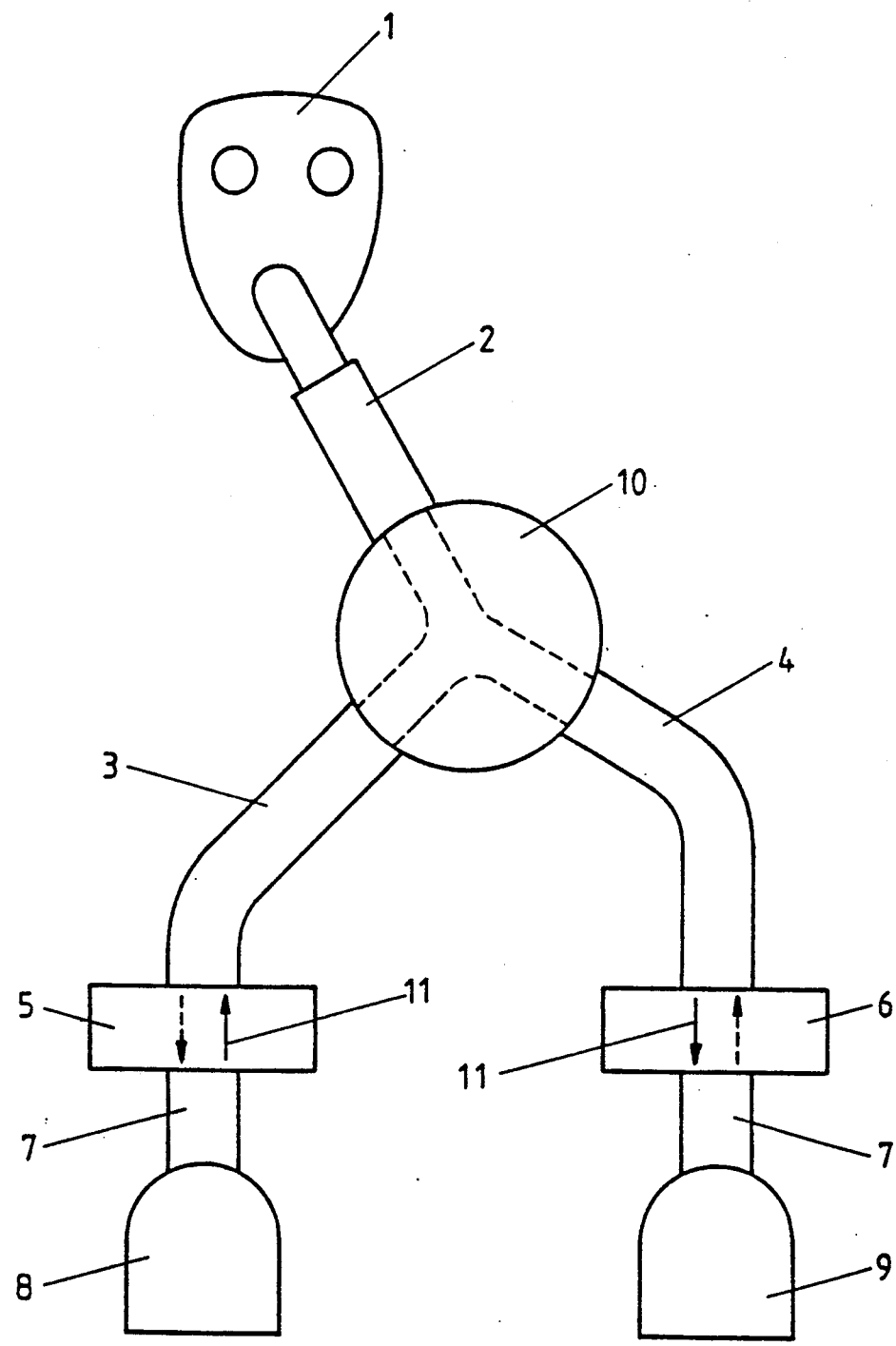
FIG. 1 is a schematic representation of the respirator with two blowers.

In FIG. 1 a respirator is schematically represented including essential components. A protective mask serving as breathing supply 1 is attached to a delivery main line 2 of a path distributor 10 to which both an inhalation branch 3 and also an exhalation branch 4 connect. The inhalation branch 3 and the exhalation branch 4 continue in an inlet blowers 5, 6 that are attached over a drying cartridge 7 to an inlet filter 8 and an outlet filter 9 respectively which connect to the surrounding atmosphere.

Figure 2:
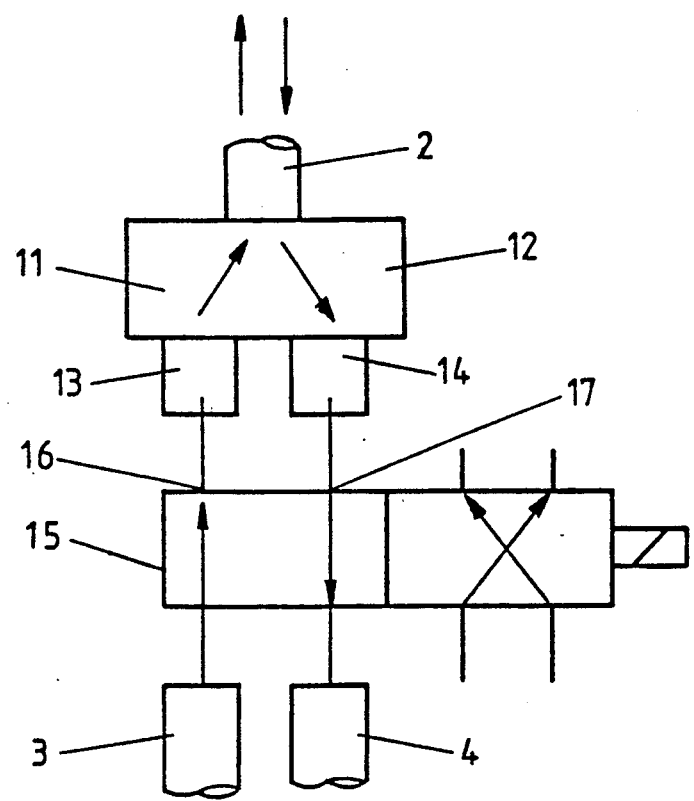
FIG. 2 is a switch valve with blower.

In FIG. 2 a circulation blower 12 is represented, having connections 13,14 to which a switch valve 15 is attached. The circulation blower 12 and switch valve 15 can be inserted together at the position of the path distributor 10 and take over the function of the individual inlet blower 5 and outlet blower 6 which can then be removed. The switch valve 15 is operable either by hand or through an electromagnetic impulse (not shown). The outlets 16,17 of the valve 15 are connected with the circulation blower 12 of the type that in the original position of the valve 15 the inlet attachment 13 of the blower 12 is connected with the inhalation branch 3 and the outlet attachment 14 with the exhalation branch. In the switched position the connection between the attachments 13,14 and the branches 3,4 will be crossed.

The depicted representation of the inhalation branch 3 and the exhalation branch 4 in FIG. 1 applies to the type of operation in which the blowers 5,6 are so switched that their delivery direction causes a flow through the filter 8,9 in the direction of the moveable direction indicator 11. Thereby the gases flow through the filter 8 from the surrounding air and the filter 8 retains the harmful substances present so that the cleansed environmental air will be delivered to the device wearer over a breathing supply 1. The exhalation air, as well as the excess quantity of transported environmental air out of the inhalation branch 3 will be blown back into the environment through the outlet blower 6 over an outlet filter 9. After a predetermined operation time of the blowers 5 and 6 in the direction of the moveable direction indicator 11 the direction of the blowers 5 and 6 will be reversed so that the flow through the filters 8 and 9 and the breathing gas leads 2,3, and 4 follow in the direction of the dotted direction indicator 11 (FIG. 1). Thereby the previous exhalation branch 4 will become a new inhalation branch, for intake of the surrounding air through the filter 7 and the excess air, as well as the exhalation air will be blown out through the filter 8. During the blowing out of the filter 8 the harmful substances absorbed in the filter material will be at least partially, if not totally desorbed and driven out of the filter 8 into the environment. Thereby the filter 8 will regenerate its filter capacity so that after repeated switching of the blower the original flowing through direction (removed arrow 11 will again be restored) the regenerated filter 8 can again serve as an inlet filter, whereby the previously loaded filter 9 will be regenerated as an outlet filter.

The same regeneration of the individual filters through alternate operation as an inlet filter and an outlet filter will be achieved through the switching arrangement according to FIG. 2. The blower 12 that is used for the inhalation branch 3 and the exhalation branch 4 delivers the air continually from the inlet attachment 13 into the outlet attachment 14. In the original position of switch valve 15 the inhalation branch 3 and the exhalation branch 4 will flow through in the shown direction. By switching the valve 5 from its original position into the switched position the gases flowing through of the inhalation branch 3 and the exhalation branch 4 will be reversed by the crossed switch paths of the vents 15 and the direction of the blower will remain unchanged.

While a specific embodiment of the invention has been shown and described in detail to illustrate the application of the principles of the invention, it will be understood that the invention may be embodied otherwise without departing from such principles.

What is claimed is:

1. A respirator with blower support, comprising: a breathing gas lead line; a first line connected to said breathing gas lead line; a second line connected to said breathing gas lead line; blower means connected to each of said first and second lines for blowing air in an inhalation direction in said first line and in an exhalation direction in said second line and said blower means periodically reversing the air flow direction to provide flow in an exhalation direction in said first line and to provide flow in an inhalation direction in said second line, said first and second lines being each connected to a filter.

2. A respirator according to claim 1, wherein said blower means includes an individual blower connected to said first line and an individual blower connected to said second line.

3. A respirator according to claim 1, whereins aid blower means includes a common blower connected to said lead line and a switching valve for switching the connection of said first line and said second line to said common blower.

4. A respirator according to claim 1, wherein drying cartridges are connected to each of said first and second line between said filter and said lead line.

5. A respirator with blower support arrangement, comprising a main breathing gas line connected to a user; a first line connected to said breathing gas line; a second line connected to said breathing gas line; a first filter connected to said first line; a second filter connected to said second line; and, blower means for generating an inhalation flow in said first line and an exhalation flow in said second line and means for periodically reversing said flow to provide an exhalation flow in said first line and an inhalation flow in said second line.

* * * * *